(12) United States Patent
Singh et al.

(10) Patent No.: US 7,732,620 B2
(45) Date of Patent: Jun. 8, 2010

(54) PROCESS FOR CRYSTALLIZATION OF RAMIPRIL AND PREPARATION OF A HYDRATED FORM THEREOF

(75) Inventors: Girij Pal Singh, Pune (IN); Umesh Babanrao Rananaware, Pune (IN); Vilas Nathu Dhake, Pune (IN)

(73) Assignee: Lupin Limited, Mambai, Maharashtra (IN)

( * ) Notice: Subject to any disclaimer, the term of this patent is extended or adjusted under 35 U.S.C. 154(b) by 470 days.

(21) Appl. No.: 10/586,542

(22) PCT Filed: Jan. 17, 2005

(86) PCT No.: PCT/IN2005/000019

§ 371 (c)(1),
(2), (4) Date: Jun. 29, 2007

(87) PCT Pub. No.: WO2005/068422

PCT Pub. Date: Jul. 28, 2005

(65) Prior Publication Data

US 2008/0171780 A1    Jul. 17, 2008

(30) Foreign Application Priority Data

Jan. 19, 2004  (IN) .......................... 56/MUM/2004

(51) Int. Cl.
*C07D 209/00*  (2006.01)
(52) U.S. Cl. ..................................................... 548/452
(58) Field of Classification Search .................. 548/452
See application file for complete search history.

(56) References Cited

U.S. PATENT DOCUMENTS

| 4,587,258 | A | | 5/1986 | Gold et al. |
| 5,061,722 | A | * | 10/1991 | Teetz et al. ................. 514/412 |
| 6,407,262 | B1 | * | 6/2002 | Wang et al. ................. 548/452 |
| 6,541,635 | B1 | | 4/2003 | Tien et al. |

FOREIGN PATENT DOCUMENTS

WO    WO 2004/064809    8/2004

* cited by examiner

*Primary Examiner*—Rei-tsang Shiao
(74) *Attorney, Agent, or Firm*—Hamre, Schumann, Mueller & Larson, P.C.

(57) ABSTRACT

The present invention relates to a novel method for obtaining (2S,3aS,6aS)-1-[(S)-2-[[(S)-1-(ethoxycarbonyl)-3-phenyl-propyl]-amino]propanoyl]octahydro cyclopenta[b]pyrrole-2-carboxylic acid, viz. Ramipril(I) in high optical purity, free of other stereoisomers, and in high bulk density. The present invention also relates to a novel hydrated form of Ramipril(I) and a process for preparation thereof.

3 Claims, 4 Drawing Sheets

Figure 1A:
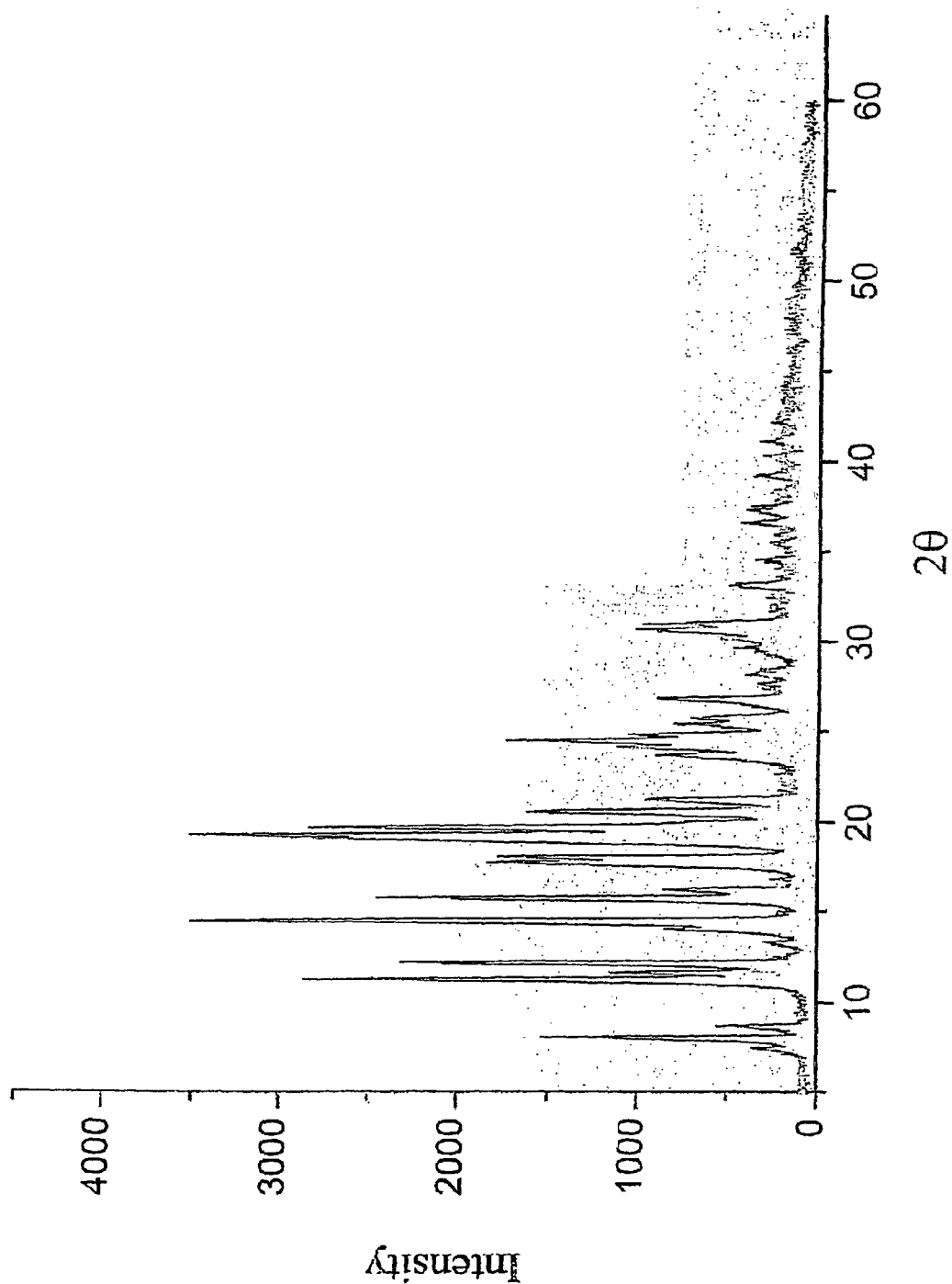

PROCESS FOR CRYSTALLIZATION OF RAMIPRIL AND PREPARATION OF A HYDRATED FORM THEREOF

FIELD OF INVENTION

The present invention relates to a novel method for obtaining (2S,3aS,6aS)-1-[(S)-2-[[(S)-1-(ethoxycarbonyl)-3-phenylpropyl]-amino]propanoyl]octahydro cyclopenta[b]pyrrole-2-carboxylic acid, viz. Ramipril(I) in high optical purity, free of other stereoisomers, and in high bulk density.

The present invention also relates to a novel hydrated form of Ramipril(I) and a process for preparation thereof.

BACKGROUND OF THE INVENTION

Ramipril(I), (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid, represented by the formula (I) is a valuable angiotensin-converting enzyme (ACE) inhibitor, a family of drugs used to treat high blood pressure and some types of heart failure.

Ramipril(I) is marketed under the brandname ALTACE®. It has five chiral centers which leads to 32 optical isomers, of which the isomer with all S-configuration exhibits highest ACE inhibiting activity. The other optical isomers are comparatively less active or are completely inactive, hence undesirable.

Ramipril(I) of formula (I) is disclosed in U.S. Pat. No. 5,061,722 (assigned to Hoechst AG) which describes a process for the preparation of Ramipril(I) comprising condensation of benzyl cis,endo-2-azabicyclo-[3.3.0]-octane-3-S-carboxylate hydrochloride of formula (II) with N-(1-S-carbethoxy-3-phenyl-propyl)-S-alanine of formula (III) in presence of a coupling agent such as dicyclohexylcarbodiimide in an organic solvent such as dimethylformamide. The diastereomeric mixture of (S,S,S,S,S) and (R,R,R,S,S) isomers of Ramipril(I) benzyl ester thus obtained is separated at this stage by silica gel chromatography using ethyl acetate/petroleum ether as the eluting solvent. The optically pure (S,S,S,S,S) benzyl ester is deprotected by hydrogenolysis or treatment with an acid or base to give Ramipril(I) of formula (I) which is on further recrystallised from ether, gives a product which has a melting point of 110-112° C.

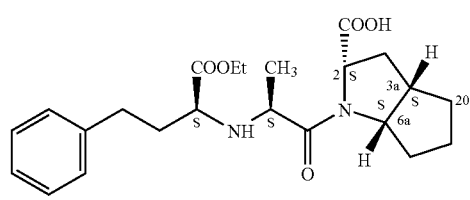

(I)

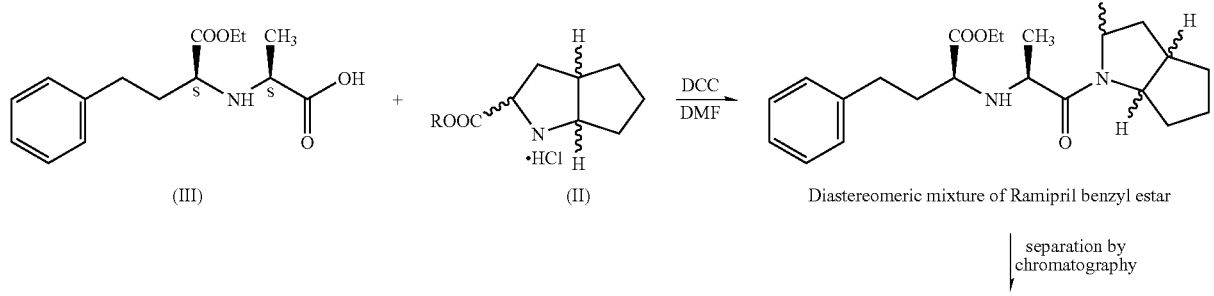

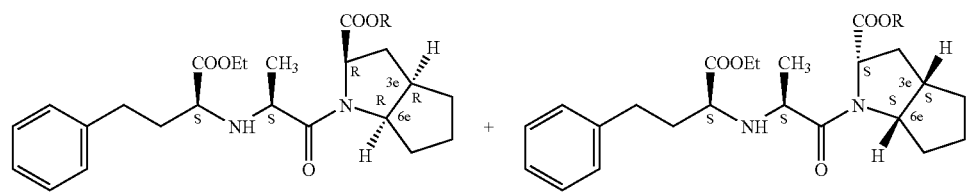

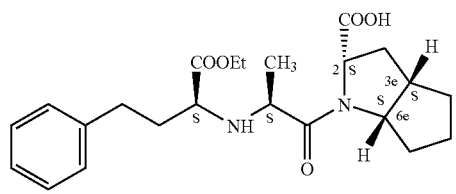

R = benzyl

Chromatographic separation of diastereomers is, however, a process of academic interest only and cannot be practiced advantageously on an industrial scale.

U.S. Pat. No. 6,407,262 (assigned to Brantford Chemicals Inc.) discloses a process for separating diastereomeric mixtures of (2S,3aS,6aS)-1-[(S)-2-[[(S)-1-(ethoxycarbonyl)-3-phenylpropyl]amino]propanoyl]octahydro-cyclopenta[b]pyrrole-2-carboxylic acid or its derivative and (2R,3aR,6aR)-1-[(S)-2-[[(S)-1-(ethoxycarbonyl)-3-phenylpropyl]amino]propanoyl]octahydro cyclopenta[b]pyrrole-2-carboxylic acid or its derivative by treating the diastereomeric mixture with a solvent or a mixture of solvents. The solvent or a mixture of solvents employed is selected from a group consisting of $C_2$-$C_4$ nitrile, $C_1$-$C_6$ alcohol, $C_6$-$C_8$ aromatic hydrocarbon, $C_3$-$C_{10}$ ether, $C_3$-$C_6$ ketone, $C_2$-$C_7$ ester, $C_1$ to $C_3$ chlorinated compounds, and $C_5$-$C_{10}$ hydrocarbon solvents.

Although, the abovementioned method claims to give Ramipril(I) of more than 99% purity, suffers from the disadvantages of utilizing the solvents which are not recommended by Regulatory and Environmental bodies, since these solvents belong to the list of Class II solvents as categorized by International Conference on Harmonization (ICH). Moreover, many of these solvents have very low flash points which render their use, on commercial scale, hazardous.

There exists a need therefore, for a method for obtaining Ramipril(I) of high optical purity which overcomes the shortcomings associated with the prior art methods.

An object of the present invention is to provide the process of preparation of optically pure Ramipril(I) having optical purity of at least 99.9% by crystallisation of optically impure Ramipril consisting of a mixture of undesired diastereomers up to 20%, from a solvent or a mixture of solvents selected from a group consisting of methyl formate, nitroalkanes, acetals and ethers.

It is another object of the present invention is to provide a novel hydrated form of Ramipril(I) which has, a distinct X-ray (powder) diffraction pattern, a distinct DSC thermogram, a distinct thermogravimetric curve and a distinct IR spectrum, which is different from the reported form of Ramipril(I).

A further object of the present invention is to provide a novel monohydrate form of Ramipril(I) having bulk density in the range of 0.2 to 0.24 g/ml.

A further object of the present invention is to provide anhydrous form of Ramipril(I) comprising of drying Ramipril monohydrate obtained above at a temperature of about 40° C. under reduce pressure of 2 to 5 mm Hg, it gives anhydrous Ramipril(I) of high bulk density (0.3-0.35 g/ml).

A further object of the invention is to provide a process for the preparation of monohydrate of Ramipril(I) comprising of crystallizing optically pure Ramipril(I) from water.

A further object of the present invention is to provide anhydrous form of Ramipril(I) comprising of drying Ramipril monohydrate obtained above at a temperature of about 40° C. under reduce pressure of 2 to 5 mm Hg, it gives anhydrous Ramipril(I) of high bulk density (0.3-0.35 g/ml).

A further object of the invention is to provide a process for the preparation of monohydrate of Ramipril(I) comprising of crystallizing optically pure Ramipril(I) from water.

SUMMARY OF THE INVENTION

Thus the present invention relates to a novel method for obtaining (2S,3aS,6aS)-1-[(S)-2-[[(S)-1-(ethoxycarbonyl)-3-phenylpropyl]-amino]propanoyl]octahydro cyclopenta[b]pyrrole-2-carboxylic acid, viz. Ramipril(I) in high optical purity, free of other stereoisomers, by a process comprising crystallizing optically impure Ramipril from a solvent or a mixture of solvents selected from a group consisting of methyl formate, nitroalkanes, acetals and ethers.

The Ramipril(I) obtained through crystallization from the abovementioned solvents or a mixture thereof has very high optical purity i.e., it is free of other stereoisomers. Further, the product so obtained exhibits improved physical characteristics such as bulk density, thermal stability, better dissolution profile, etc. which renders it highly suitable for formulation into a suitable dosage form.

For the purpose of this specification optically pure Ramipril(I) is defined as Ramipril(I) having optical purity of at least 99.9%, which is having all the chiral carbon centres in the S-configuration and, is free from other undesired stereoisomers.

Accordingly, the present invention provides the process of preparation of optically pure Ramipril(I) having optical purity of at least 99.9%.

According to a preferred aspect the process for the preparation of optically pure Ramipril(I) having optical purity of at least 99.9% comprises crystallisation of optically impure Ramipril consisting of a mixture of undesired diastereomers up to 20%, from a solvent or a mixture of solvents selected from a group consisting of methyl formate, nitroalkanes, acetals and ethers.

Although when the optically impure Ramipril is crystallised from highly polar hydroxyl solvents it does not form any hydrates even with methanol nor it forms any solvates with solvent having high dipole moment such nitromethane, but it has been surprisingly found that impure Ramipril when crystallized from a mixture of water and water immicible solvents, a 1:1 solvate i.e. hydrate form of Ramipril(I) having all the carbons in the S-configuration, crystallised out leaving all the other stereoisomer behind in the solvent i.e. in the filtrate.

It is further surprisingly found that if the Ramipril(I) monohydrate obtained above is dried at a temperature of 40° C. under reduced pressure of 2 to 5 mm Hg, it gives anhydrous Ramipril(I) of high bulk density (0.3-0.35 g/ml)

In another aspect of the present invention there is provided a novel hydrated form of Ramipril(I) which has, a distinct X-ray (powder) diffraction pattern, a distinct DSC thermogram, a distinct thermogravimetric curve and a distinct IR spectrum, which is different from the reported form of Ramipril(I).

According to a further aspect of the present invention there is provided a novel monohydrate form of Ramipril(I) having bulk density in the range of 0.2 to 0.24 g/ml.

In a further aspect, the present invention relates to a novel monohydrate form of Ramipril(I) and a process for preparation thereof comprising of crystallizing optically impure Ramipril from a mixture of water and water-immiscible solvents.

DETAILED DESCRIPTION OF THE DRAWINGS

FIG. 1a: The X-ray (Powder) diffraction pattern of the Ramipril hydrate obtained by the process of the present invention.

Figure 1B:
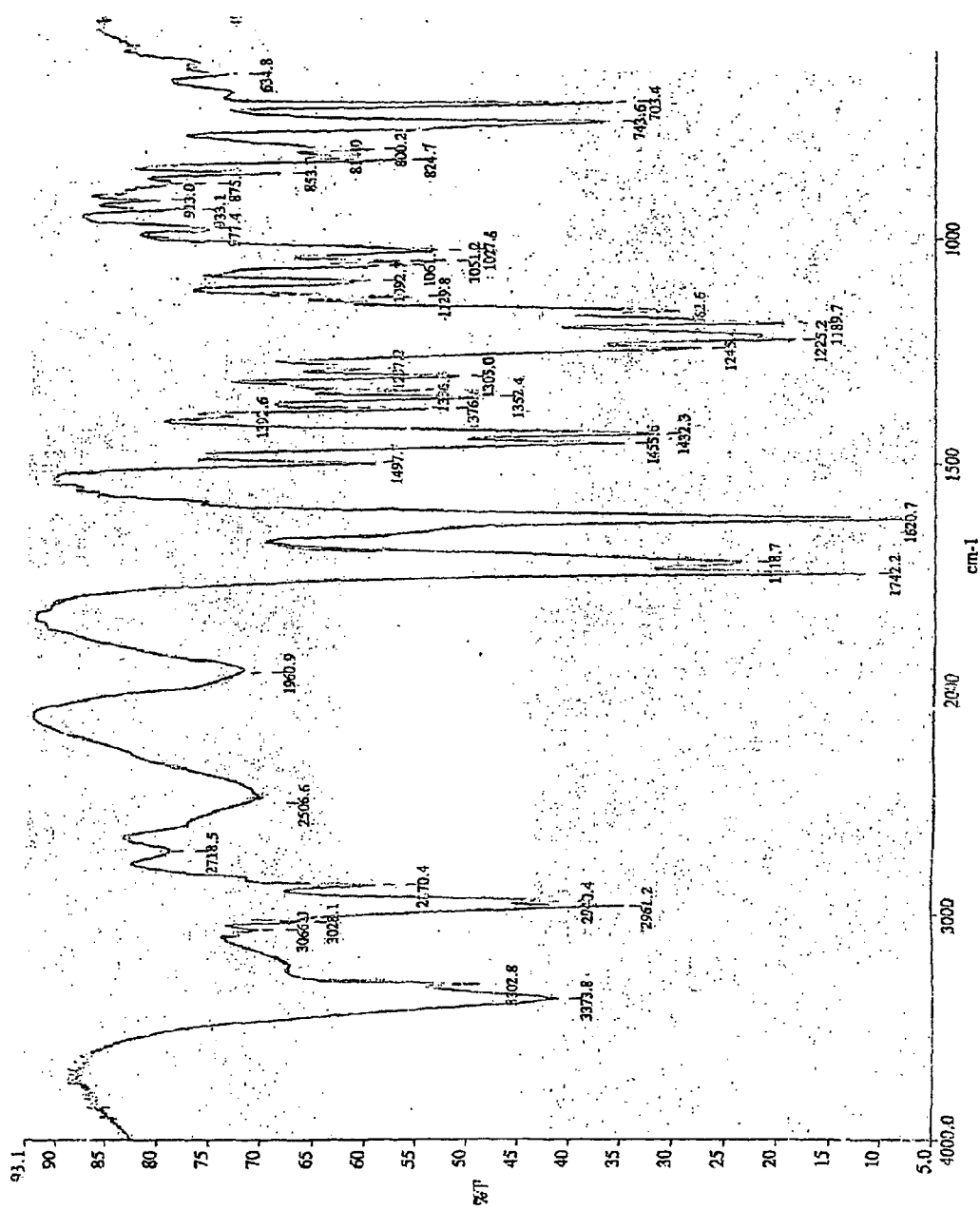

FIG. 1b: The IR Spectrum of the Ramipril hydrate obtained by the process of the present invention.

Figure 1C:
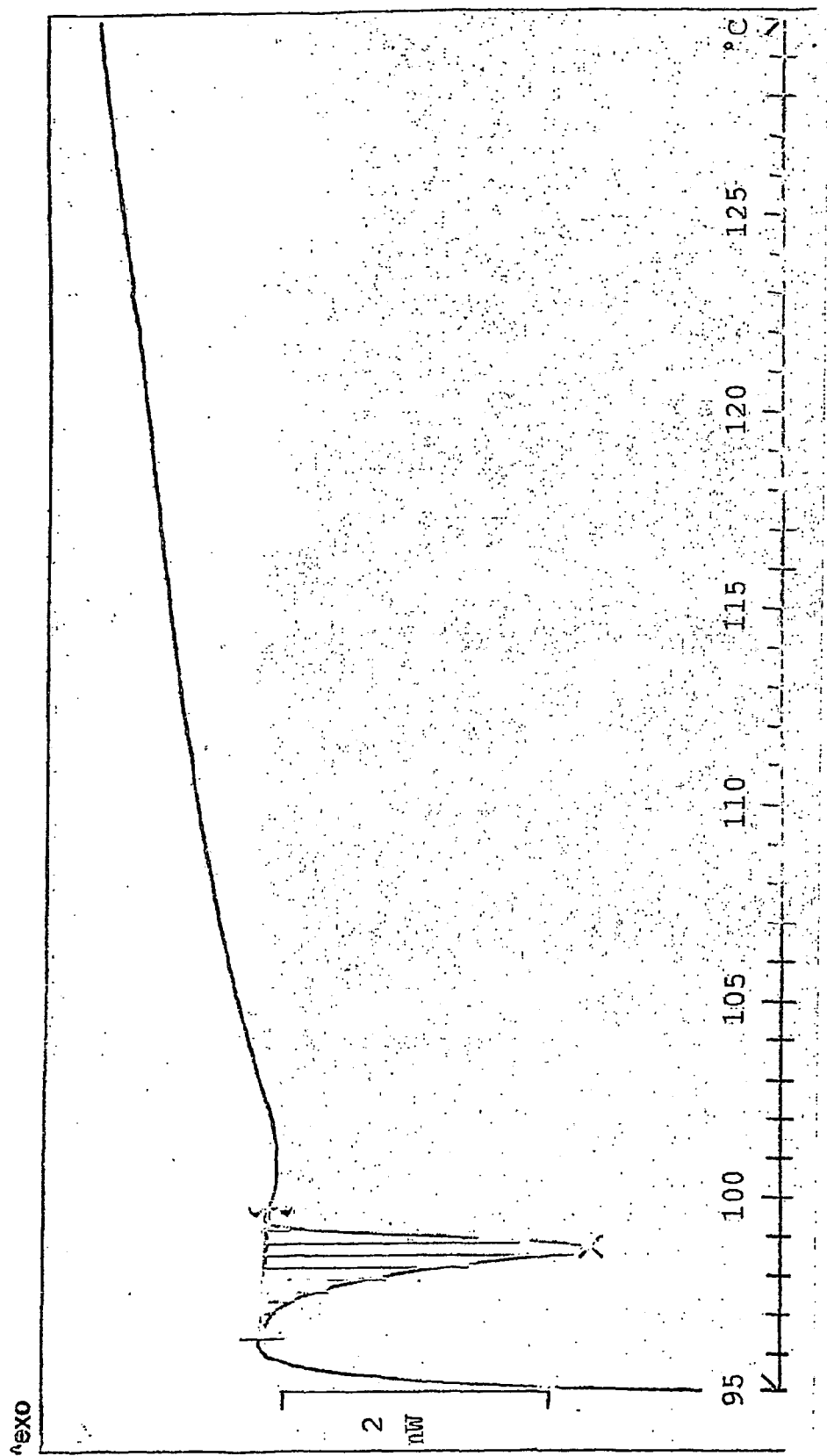

FIG. 1c: The DSC thermogram of the Ramipril hydrate obtained by the process of the present invention.

Figure 1D:
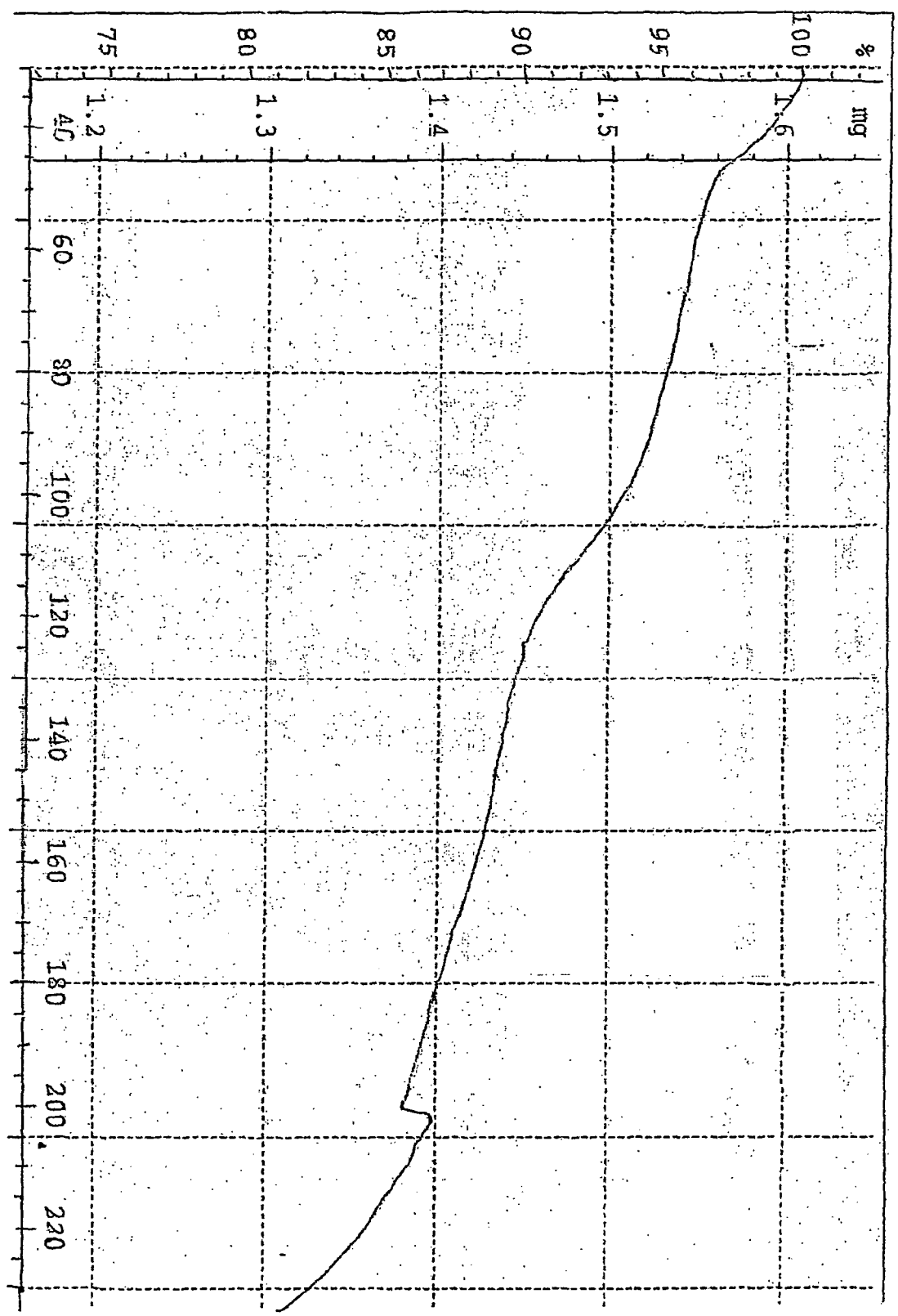

FIG. 1d: The TGA thermogram of the Ramipril hydrate obtained by the process of the present invention.

DETAILED DESCRIPTION OF THE INVENTION

The present invention provides a novel method for obtaining Ramipril(I) in high optical purity, free of other stereoisomers, and having high bulk density, comprising of crystallizing optically impure Ramipril from a solvent or a mixture thereof.

The solvents are selected from a group consisting of aliphatic esters such as methyl formate, nitroalkanes such as nitromethane and acetals, such as dimethoxymethane, diethoxymethane and 2,2-dimethoxy propane.

Typically, one of the above solvents or a mixture thereof is added to the optically impure Ramipril consisting of a mixture of undesired diastereomers up to 20% and the solution is stirred at 20-25° C. for 20-50 minutes, cooled to −10 to 10° C. and stirred again for 2-5 hrs. The solid product which separates out is filtered, washed with cold solvent and dried. The product so obtained has an optical purity of 99.9%.

The compact, crystalline Ramipril(I), so obtained, has a bulk density in the range from 022 to 0.24 g/ml which is the most suitable for pharmaceutical preparations.

The bulk density is an economically, commercially, and functionally important property. High bulk density of the active pharmaceutical compound facilitates compression of tablets and filling of capsules. Additionally, very good flowability can be obtained with high-bulk-density powders. Moreover, when shipping powders over long distances a high bulk density results in reducing the shipping volume. A high bulk density compound also saves packing material and storage capacity.

A comparison of the bulk density (BD), tapped density (TD) and melting point of Ramipril(I) obtained by using various solvents of present invention and of prior-art process is summarised in Table-I hereinbelow.

TABLE I

Comparison of the physical properties of Rampril obtained by the Prior Art methods and the method of the present invention

| Method | Solvent | B.D. (g/ml) | T.D. (g/ml) | M.P. (° C.) |
|---|---|---|---|---|
| Prior art | Ethanol-diisopropyl ether | 0.08-0.1 | 0.13-0.15 | 105.6-106.4 |
|  | Ethanol-diethyl ether | 0.09-0.12 | 0.15-0.17 | 105.5-107 |
| Present invention | Diethoxymethane | 0.22-0.24 | 0.32-0.37 | 105.6-107.2 |
|  | Methyl formate | 0.11-0.13 | 0.15-0.17 | 106-108 |
|  | 2,2-Dimethoxy-propane | 0.1-0.13 | 0.14-0.18 | 104.7-105.7 |
|  | Nitromethane | 0.12-0.14 | 0.15-0.17 | 104.8-105.4 |

Table II depicts the stability data of Ramipril(I) crystallized by diethoxymethane which shows that the Ramipril(I) obtained through crystallization from the abovementioned solvents or a mixture thereof exhibits acceptable physical characteristics such as stability.

TABLE II

Stability Data of Ramipril(I), crystallized by Diethoxymethane

| | | | | Temp/RH 40° C. ± 2° C./75% ± 5% | | |
|---|---|---|---|---|---|---|
| Sr. No. | Test | Solvent | Initial | 1 Month | 2 Month | 3 Month |
| 1 | Assay by HPLC(%) | Diethoxy methane | 99.68 | 99.5 | 99.2 | 99.12 |

Further, the X-Ray diffraction pattern of the optically pure Ramipril(I) obtained as mentioned hereinabove is found to be identical to X-ray powder diffraction pattern of the product obtained by following the procedure given in Example 1 (column 6, line 25) of the U.S. Pat. No. 5,061,722 (assigned to Hoechst AG).

In another aspect, the present invention relates to a novel hydrate of Ramipril(I) and a process for preparation thereof, comprising, crystallizing optically impure Ramipril from a mixture of water and water immiscible solvents.

The novel hydrate of Ramipril(I) occurs in crystalline form. It is readily converted to the anhydrous moiety by heating at a temperature in the range from 40° C. to 42° C. under reduced pressure of 2 to 5 mm hg. The novel hydrate form is stable up to a temperature of 25° C. The monohydrate is transformed into anhydrous Ramipril(I), the so-called "anhydrate" on heating above 40° C. with a speed depending on the conditions of dehydration.

A typical process for the preparation of the hydrated form of Ramipril(I) comprises dissolving Ramipril(I) in a lower aliphatic alcohol such as ethanol and agitating it at a temperature in the range of 25 to 30° C. to get a clear solution. The solvent is then removed completely and a mixture of water and a water-immiscible solvent is added to the oily residue. The solution is stirred at a temperature in the range from 25 to 30° C. The solid which crystallized out is cooled, filtered and washed with water or water-immiscible solvent. The solid is dried under reduced pressure at 10-25° C.

The water immiscible solvents used for the above process include but are not limited to ethers like diisopropyl ether, acetals such as diethoxymethane and 2,2-dimethoxy propane, hydrocarbons such as cyclohexane, ketones such as methyl isobutyl ketone and esters such as ethyl acetate.

In case of a mixture of water and water-immiscible solvent employed for the abovementioned process, the water immiscible solvent can be added in a ratio of about 2 to 98% w/w of water, more preferable a ratio 90-95% w/w of water-immiscible solvent to water.

The Ramipril(I) monohydrate having a water content between 4 to 4.5%, so obtained, exhibits improved physical characteristics such as, improved bulk density in the range of 0.2 to 0.24 g/ml and tapped density in the range of 0.3 to 0.5 g/ml as compared to the samples prepared by following the procedure given in Example 1 (column 6, line 25) of the U.S. Pat. No. 5,061,722 (assigned to Hoechst AG), which has a bulk density of 0.09 to 0.12 g/ml and tapped density of 0.15 to 0.17 g/ml. The novel hydrate with improved bulk density has a better flowability and hence is most suitable for pharmaceutical preparations.

The monohydrate recrystallized from only water also has a different crystal structure. Ramipril(I) monohydrate prepared by recrystallized from only water as per the present invention is a fine lath like crystalline solid. The more regular size and shape of the Ramipril(I) monohydrate is expected to impart improved flow characteristics and so aid tablet or capsule manufacture compared to the long needle-like structures of Ramipril(I) anhydrate.

The novel hydrated from of Ramipril(I) has DSC thermogram, X-ray (powder) diffraction pattern, thermogravimetric curve and IR spectrum distinctly different from Ramipril(I) of prior art methods.

The present invention provides a novel hydrate of Ramipril (I), having a powder x-ray diffractogram substantially as depicted in FIG. 1a, with characteristic peaks at X-ray powder diffraction pattern with the diffraction angle (2 θ) and relative intensity as given in Table-III.

TABLE III

Diffraction angle (2 θ) and Relative intensity (%) of Ramipril(I) monohydrate

| Diffraction angle 2 θ | Relative Intensity (%) |
|---|---|
| 8.7 | 16 |
| 9.2 | 3 |
| 9.4 | 3 |
| 9.7 | 3 |
| 11.2 | 81 |
| 11.6 | 33 |
| 12.2 | 66 |
| 14.54 | 96 |
| 15.7 | 70 |
| 18.0 | 51 |
| 19.7 | 81 |
| 24.5 | 49 |
| 24.8 | 30 |

The powder x-ray diffraction pattern were recorded on a Philips analytical X-ray B.V. The diffractometer type was PW1710 BASED. The tube anode was copper. The wave length used was 1.54439 A°. The intensity ratio was 0.5. The type of scan was a continuous one.

The novel hydrate form of Ramipril(I) has significant IR bands at 3372, 3302, 2961, 2940, 2871, 2504, 1961, 1742, 1718, 1621, 1456, 1432, 1246, 1225, 1190, 1163, 1028, 743 and 704 cm$^{-1}$. The IR spectrum is as depicted in FIG. 1b. The IR spectrum was recorded using a Shimadzu FTIR 8201 PC.

Representative DSC thermogram for the hydrated form of Ramipril(I) is shown in FIG. 1c.

Analysis by DSC shows characteristic peaks between at 94° C. and 99° C. DSC data were generated using a Mettler-Toledo DSC 820. In general, samples were analysed in a vented, sealed aluminum pan. Because the endothermic peak may vary depending upon the rate of heating and the calibration and precision of the instrument, with the amount of peak variation dependent upon the heating rate used, all thermograms included herein were run under the same, consistent conditions heating at 1° C. per minute under a nitrogen purge a 40 mL per minute.

Thermogravimetric analysis for the novel hydrate form as shown in FIG. 1d indicates a mass loss of 4.1% between 40° and 70° C., which corresponds to one molecule of water per one molecule of Ramipril(I).

In another aspect of the invention it provides a process for the preparation of monohydrate of Ramipril(I) comprising of crystallizing optically pure Ramipril(I) from water.

The following examples serve to illustrate the invention, but however, should not be construed as limiting the scope of the invention.

EXAMPLE 1

Synthesis of Ramipril(I) and Crystallization of Ramipril(I) by Utilizing Diethoxymethane A enantiomeric mixture of benzyl cis, endo-2-azabicyclo-[3.3.0]-octane-3-S-carboxylate, wherein the SSS:RRR ratio is 87:13, (100 g), and dichloromethane (500 ml) was charged to a round bottom flask. Demineralized water (100 ml) was added to it and the mixture was stirred for 15 minutes at 25-30° C. A 10% aqueous solution of sodium carbonate was then added till the pH of the solution reached 9.5-10.0 at 15-20° C. and the solution became clear. The mixture was stirred for 60 minutes to dissolve the solid.

The layers were separated and the organic layer was washed twice with 5% aqueous sodium carbonate solution (300 ml). The aqueous layer is extracted 2 or 3 times with dichloromethane (150 ml).

The organic layers are combined and washed with demineralized water. The organic layer is separated and added slowly to a solution of N-(1(s)-ethoxycarbonyl-3-phenylpropyl)-L-alanine N-carboxyanhydride (NEPA-NCA) in dichloromethane (400 ml) over a period of 30-60 minutes at 20-25° C. The reaction mixture was stirred for 120-180 minutes at 20-25° C., till the reaction was completed.

A 10% solution of sodium carbonate (300 ml) and triethylamine (5 ml) were added to the reaction mixture and the solution was stirred for 120-240 minutes at 20-25° C. to hydrolyze the unreacted NEPA-NCA.

The organic layer was washed twice with 5% aqueous sodium carbonate (300 ml) and then with demineralized water (200 ml×2). The organic layer was separated and charcoal (10 g) was added to it and stirred for 30 min at 25-30° C. The charcoal residue was filtered and washed twice with dichloromethane (25 ml).

The mixture was concentrated in vacuum at 30 to 35° C., and 10 g of the residue, containing a mixture of 98% (SSSSS) and 2% (RRRSS) benzyl N-(2-S-carbethoxy-3-phenyl-propyl)-S-alanyl-cis, endo-2-azabicyclo-[3.3.0]-octane-3-S-carboxylate, was taken up in ethanol (30 ml), 0.5 g of 10% Pd/C was added and hydrogenation was carried out at 50-55 psi at 20-25° C. On completion of the reaction, the catalyst was filtered and washed with ethanol (30 ml).

The filtrate was concentrated and the residue was dissolved in diethoxymethane (100 ml). The solution was stirred at 20-25° C. for 30 minutes, cooled to 0-5° C. and further stirred for a period of 180-240 minutes. The crystallized solid was filtered, washed with cold diethoxymethane (50 ml) and dried for 15-18 h at 35-37° C. under reduced pressure (2-5 mm Hg). Crystalline Ramipril(I) having optical purity of 99.9% in a yield of 85%. Melting point is in the range of 106° C. to 108° C.

EXAMPLE 2

Synthesis of Ramipril(I) and Crystallization of Ramipril(I) by Utilizing Nitromethane A enantiomeric mixture of benzyl cis, endo-2-azabicyclo-[3.3.0]-octane-3-S-carboxylate, wherein the SSS:RRR ratio is 87:13, (100 g), and dichloromethane (500 ml) was charged to a round bottom flask. Demineralized water (100 ml) was added to it and the mixture was stirred for 15 minutes at 25-30° C. A 10% aqueous solution of sodium carbonate was then added till the pH of the solution reached 9.5-10.0 at 15-20° C. and the solution became clear. The mixture was stirred for 60 minutes to dissolve the solid.

The layers were separated and the organic layer was washed twice with 5% aqueous sodium carbonate solution (300 ml). The aqueous layer is extracted 2 or 3 times with dichloromethane (150 ml).

The organic layers are combined and washed with demineralized water. The organic layer is separated and added slowly to a solution of N-(1(s)-ethoxycarbonyl-3-phenylpropyl)-L-alanine N-carboxyanhydride (NEPA-NCA) in dichloromethane (400 ml) over a period of 30-60 minutes at 20-25° C.

The reaction mixture was stirred for 120-180 minutes at 20-25° C., till the reaction was completed. A 10% solution of sodium carbonate (300 ml) and triethylamine (5 ml) were added to the reaction mixture and the solution was stirred for 120-240 minutes at 20-25° C. to hydrolyze the unreacted NEPA-NCA.

The organic layer was washed twice with 5% aqueous sodium carbonate (300 ml) and then with demineralized water (200 ml×2). The organic layer was separated and charcoal (10 g) was added to it and stirred for 30 min at 25-30° C. The charcoal residue was filtered and washed twice with dichloromethane (25 ml).

The mixture was concentrated in vacuum at 30 to 35° C., and 10 g of the residue, containing a mixture of 97% (SSSSS) and 3% (RRRSS) benzyl N-(2-S-carbethoxy-3-phenyl-propyl)-S-alanyl-cis, endo-2-azabicyclo-[3.3.0]-octane-3-S-carboxylate, was taken up in ethanol (30 ml), 0.5 g of 10% Pd/C was added and hydrogenation was carried out at 50-55 psi at 20-25° C. On completion of the reaction, the catalyst was filtered and washed with ethanol (30 ml).

The filtrate was concentrated and the residue was dissolved in nitromethane (100 ml). The solution was stirred at 20-25° C. for 30 minutes, cooled to 0-5° C. and further stirred for a period of 180-240 minutes. The solution was cooled to −5 to −10° C. and maintained at that temperature overnight. The crystallized solid was filtered, washed with cold nitromethane (50 ml) and dried for 15-18 h at 35-37° C. under reduced pressure (2-5 mm Hg). Crystalline Ramipril(I) having optical purity of 99.9% in a yield of 75%. Melting point is in the range of 106° C. to 108° C.

EXAMPLE 3

Preparation of Ramipril(I) Monohydrate by Crystallizing from Mixture of Water and Diethoxymethane A diastereomeric mixture of 98% (SSSSS) and 2% (RRPSS) Ramipril(I) (6.0 g) and ethanol (60 ml) was stirred at room temperature to get a clear solution. The ethanol is evaporated under pressure at 30-35° C. To the sticky, oily residue was added a mixture of Diethoxymethane (60 ml) and water (4.98 ml). The mixture is stirred slowly for 60 to 90 minutes till all the Ramipril(I) Monohydrate crystallizes out. The slurry is cooled to 5-10° C. and maintained at that temperature for 30 minutes. The solid is filtered, washed with cold diethoxymethane and dried at 25° C. for 18-20 h under reduced pressure (2-5 mm Hg). Yield: 85%. The water content of the product was 4.08%. Purity by HPLC is 99.90%. Melting point is in the range from 94-98° C. X-ray powder diffraction pattern is as summarized in FIG. 1a. DSC thermogram as described in FIG. 1c. TGA thermogram is as summarized in FIG. 1d.

EXAMPLE 4

Preparation of Ramipril(I) Monohydrate by Crystallizing from Mixture of Water and Diisopropylether A diastereomeric mixture of 98% (SSSSS) and 2% (RRRSS) Ramipril(I) (6.0 g), and ethanol (60 ml) was stirred at room temperature to get a clear solution. The ethanol is evaporated under pressure at 30-35° C. To the sticky, oily residue was added a mixture of diisopropylether (60 ml) and water (0.87 ml). The mixture is stirred slowly for 60 to 90 minutes till all the Ramipril(I) Monohydrate crystallizes out. The slurry is cooled to 5-10° C. and maintained at that temperature for 30 minutes. The solid is filtered, washed with cold diisopropylether and dried at 25° C. for 18-20 h under reduced pressure (2-5 mm Hg). Yield: 85%. The water-content of the product was 4.1%. Purity by HPLC is 99.90%. Melting point is in the range from 94-98° C. X-ray powder diffraction pattern is as summarized in FIG. 1a. DSC thermogram as described in FIG. 1c. TGA thermogram is as summarized in FIG. 1d.

EXAMPLE 5

Preparation of Ramipril(I) Monohydrate by Crystallizing from Water

An optically pure Ramipril(I) (6.0 g), and ethanol (60 ml) was stirred at room temperature to get a clear solution. The ethanol is evaporated under pressure at 30-35° C. To the sticky, oily residue was added water (60 ml). The mixture is stirred slowly for 60 to 90 minutes till all the Ramipril(I) Monohydrate crystallizes out. The slurry is cooled to 5-10° C. and maintained at that temperature for 30 minutes. The solid is filtered, washed with cold water and dried at 25° C. for 18-20 h under reduced pressure (2-5 mm Hg). Yield: 86%. The water content of the product was 4.18%. Purity by HPLC is 99.90%. Melting point is in the range from 94-98° C. X-ray powder diffraction pattern is as summarized in FIG. 1a. DSC thermogram as described in FIG. 1c. TGA thermogram is as summarized in FIG. 1d.

EXAMPLE 6

Preparation of Anhydrous Ramipril(I) from Monohydrate Ramipril(I)

Ramipril(I) monohydrate (6.0 g) obtained from example 5 is charged in a petridish. Kept this Ramipril(I) monohydrate in a vacuum oven and dry at 40° C. under reduced pressure (2 mm Hg) for 10-12 hours. The material kept open in air for 12 hours and unloaded. The product obtained is an anhydrous form of Ramipril(I). Yield: 94%. Melting point of product obtained was 105° C.

EXAMPLE 7

Comparison of Dissolution Profile of Ramipril(I) Crystallized from Diethoxymethane as Well as the Ramipril(I) Monohydrate Optically pure Ramipril(I) obtained from example 1 is formulated as a solid pharmaceutical composition by conventional way of direct mixing process with excipients such as pregelatinized starch.

Ramipril(I) monohydrate obtained from example 5 is formulated as a solid pharmaceutical composition by conventional way of direct mixing process with excipients such as pregelatinized starch.

The in vitro drug release profile was carried out using USP apparatus 1,500 ml of 0.1 N HCl at 50 RPM. Following table provides a comparison of dissolution profile of Ramipril(I) crystallized from diethoxymethane as well as the Ramipril(I) monohydrate and prior art method.

TABLE III

| | % Drug release of the Label claim | | | |
|---|---|---|---|---|
| Time (Min.) | Prior art Method | Innovator (Altace) | Crystallised from Diethoxymethane | Monohydrate Ramipril(I) |
| 5 | 18.8% | 56.8 | 48.4% | 40.8% |
| 10 | 75% | 77.4% | 93.8% | 87% |

The invention claimed is:

1. A process for purification of optically impure Ramipril to obtain Ramipril(I) having the chemical formula (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid of formula (1)

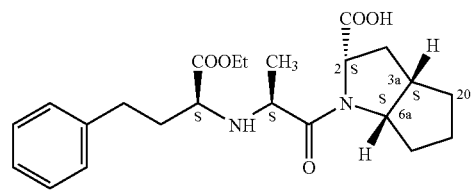

having optical purity of at least 99.9%, which comprises crystallizing optically impure Ramipril from an organic solvent selected from nitromethane, dimethoxymethane, diethoxymethane, and 2,2,-dimethoxy propane and mixtures thereof.

2. The process as claimed in claim 1 wherein the organic solvent is diethoxymethane.

3. The process as claimed in claim 1, wherein the optically pure Ramipril(I) is obtained by the process consisting essentially of the crystallizing from the organic solvent.

* * * * *